United States Patent [19]

Lo et al.

[11] Patent Number: 5,130,439

[45] Date of Patent: Jul. 14, 1992

[54] TETRAZOLYLPHENYLBORONIC ACID INTERMEDIATES FOR THE SYNTHESIS OF AII RECEPTOR ANTAGONISTS

[76] Inventors: Young S. Lo, 516 Stenning Dr., Hockessin, Del. 19707; Lucius T. Rossano, 7 West Ridge Ct., Newark, Del. 19711

[21] Appl. No.: 793,514

[22] Filed: Nov. 18, 1991

[51] Int. Cl.$^5$ .......................................... C07D 257/02
[52] U.S. Cl. ................................................ 548/110
[58] Field of Search ......................................... 548/110

[56] References Cited

PUBLICATIONS

CA 98:89140q Reactions of . . . bond systems. Scherowsky et al. p. 537, 1983.

*Primary Examiner*—Mary C. Lee
*Assistant Examiner*—Joseph K. McKane

[57] ABSTRACT

Novel tetrazolylphenylboronic acids, methods for their preparation, and their use in the syntheses of angiotensin II receptor antagonists are disclosed.

6 Claims, No Drawings

TETRAZOLYLPHENYLBORONIC ACID INTERMEDIATES FOR THE SYNTHESIS OF AII RECEPTOR ANTAGONISTS

BACKGROUND OF THE INVENTION

1. Field of the Invention

This invention is concerned with novel tetrazolylphenylboronic acids and their derivatives, methods for their preparation and their use in processes for the preparation of angiotensin II receptor antagonists which are effective agents for the treatment of hypertension and congestive heart failure.

2. Background and Prior Art

The successful development of orally active angiotensin converting enzyme (ACE) inhibitors, e.g., captopril, enalapril, etc., for the treatment of hypertension and congestive heart failure has generated great interest in designing new pharmacological blockers of the renin-angiotensin system (RAS). As angiotensin II (AII) is the primary effector molecule of the RAS (Peach, J. J., Renin-Angiotensin System:Biochemistry and Mechanism of Action, Physiol. Rev., 1977, 57:313-370), a receptor antagonist of AII would provide a direct approach to block the system. A number of peptide analogs of AII have been reported to have AII receptor antagonist properties; however, they also retain partial agonist properties and lack oral activities (Corvol, P., New Therapeutic Prospects of Renin-Angiotensin System Inhibition, Clin. Exp. Hypertens.-Theory & Practice, 1989, AII (Suppl. 2), 463-470). More recently, following the disclosure of a few nonpeptide AII antagonist leads (U.S. Pat. No. 4,355,040), several series of AII antagonists have been synthesized at E. I. du Pont de Nemours and Company. Many of these compounds are orally active with potent activities (Wong, P. C., et al., Functional Studies of Nonpeptide Angiotensin II Receptor Subtype-Specific Ligands:DuP753 (AII-1) and DP123177 (AII-2), J. Pharm. and Exp. Ther., 1990, 255 (2), pp 584 to 592 and references therein). These novel compounds were disclosed in European Patent Application 0 324 377 published Jul. 19, 1989.

Many of the AII receptor antagonists have the biphenyl structure as a portion of the molecule. Synthetic methods for the preparations of biphenyls were reviewed recently (Bringmann, G., et al., Angew. Chem. Int. Ed. Engl., 29, 1990, 977 to 991). Also Duncia, et al. (U.S. Pat. No. 4,820,843 and J. Org. Chem., 1991, 56, 2395-2400) described alternate preparations of biphenyls. The preparation, properties, and uses of boronic acids and derivatives were summarized in Metal-Organic Compounds, Advances in Chemistry Series, #23, American Chemical Society, 1959. The ortho-lithiation of 2-substituted 5-phenyl-tetrazoles was disclosed in U.S. Pat. No. 5,039,814.

SUMMARY OF THE INVENTION

The novel tetrazolylphenylboronic acid derivatives prepared in accordance with this invention are represented by formula I below

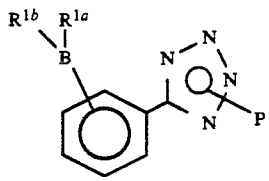

wherein:

P is triphenylmethyl, tertiary-butyl, $C_1$–$C_4$ alkoxymethyl, methylthiomethyl, phenyl $C_1$–$C_4$ alkoxymethyl, p-methoxybenzyl, 2,4,6-trimethylbenzyl, 2-(trimethylsilyl)ethyl, tetrahydropyranyl, piperonyl, or benzenesulfonyl; and $R^{1a}$ and $R^{1b}$ are each independently chlorine, bromine, $C_1$–$C_4$ alkoxy or hydroxy; and $R^{1a}$ and $R^{1b}$ can be taken together with B to form a cyclic structure

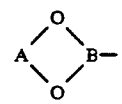

where A is phenyl, or $(CH_2)_n$, where n is 2–4.

The novel compounds of formula I are prepared by reacting a compound represented by the formula

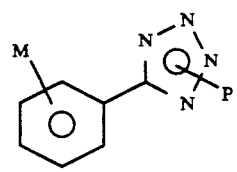

wherein:

P is defined as for formula I above; and

M is a metal selected from the group consisting of lithium, sodium, potassium, or magnesium with a boron compound having the formula

wherein $R^{1a}$ and $R^{1b}$ are as defined for formula I above and $R^{1c}$ is chlorine, bromine or $C_{1-4}$ alkoxy.

The novel tetrazolylphenylboronic acids or derivatives represented by formula I can be reacted further to provide more advanced intermediates that are precursors for AII receptor antagonists. Thus, the compounds of formula I are employed in a cross-coupling reaction with substituted phenyl compounds represented by the formula

wherein

X is bromine, iodine, methanesulfonyloxy, toluenesulfonyloxy, fluorosulfonyloxy, or trifluoromethanesulfonyloxy; and Q is hydrogen, methyl, $C_1$–$C_4$ alkyl, hydroxymethyl, triorganosilyloxymethyl, hydroxy $C_1$–$C_4$ alkyl, formyl, $C_1$–$C_4$ acyl, $C_1$–$C_4$ alkoxycarbonyl, or W-L-wherein L is a single bond, —$(CH_2)_t$ where t is 1 to 4, —$(CH_2)_r$O$(CH_2)_r$—, —$(CH_2)_r$S(O)$_r$— where r is 0 to 2 and W is a mono-, bi-, or multi-cyclic heteroaromatic group, which may be partially or completely hydrogenated, in which each ring member of said group includes at least 1 carbon atom and from 1 to 5 heteroatoms. For purposes of the present invention, preferably W is a group of the following formula:

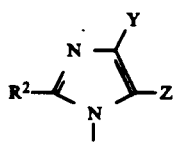

wherein $R^2$ is $C_1$–$C_4$ alkyl, Y is $C_1$–$C_4$ alkyl, $C_1$–$C_4$ perfluoroalkyl, halogen, phenyl unsubstituted or substituted with one or two substituents selected from $C_1$–$C_4$ alkyl, F, Cl, $CF_3$, $C_1$–$C_4$ alkoxyl, phenoxyl, phenyl; phenyl $C_1$–$C_4$ alkyl and Z is hydroxymethyl, formyl, $C_1$–$C_4$ acyl, $C_1$–$C_4$ alkoxylcarbonyl, carboxyl; and where Y and Z can be taken together to form a 5-, 6-, or 7-membered ring containing 1 to 2 heteroatoms selected from nitrogen, sulfur, or oxygen.

The products of this cross-coupling reaction are compounds of the formula

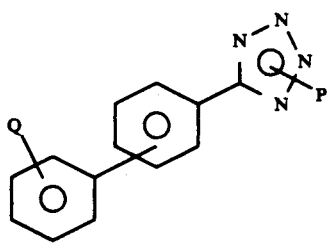

wherein P and Q have the meanings given above and the position of

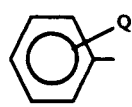

relative to the tetrazole is the same as the position of

relative to the tetrazole in formula I.

Thus an overall reaction scheme contemplated as a part of this invention can be presented by the following

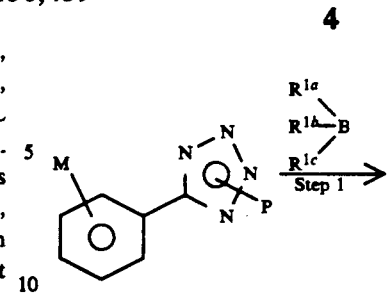

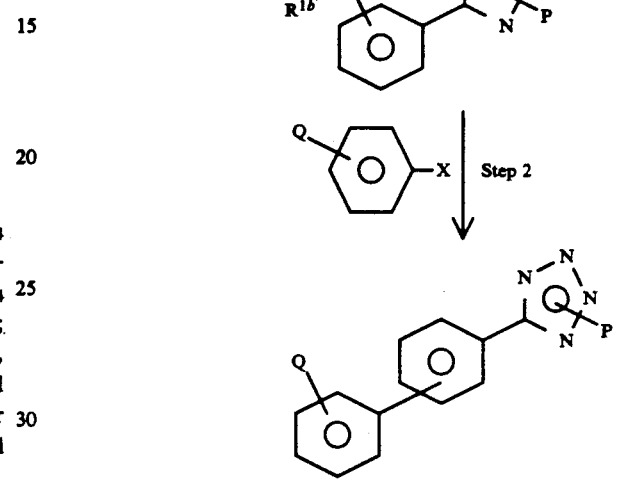

wherein M, X, P, $R^{1a}$, $R^{1b}$, $R^{1c}$ and Q have the meanings given above.

It is therefore an object of the present invention to provide novel and efficient processes for the preparation of novel tetrazolylphenylboronic acids and derivatives, and the preparation of more advanced intermediates of AII receptor antagonists in subsequent reactions.

Additional objects and advantages of the present invention will be apparent to one skilled in the art and still others will become apparent from the following description for carrying out the present invention and the appended claims.

DETAILED DESCRIPTION OF THE INVENTION

In step 1 of the overall reaction scheme shown above the carbanion having the formula

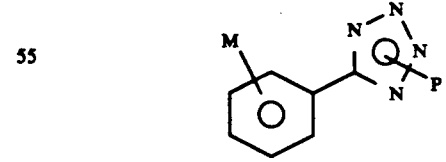

and the boron compound having the formula

are reacted together.

The meanings given above for P, the protecting group for the tetrazole substituent in formula I are those considered the most preferred for purposes of the invention. However, since tetrazoles are isosteric with carboxyl groups and the protecting group is blocking a nitrogen, many of the protecting groups used for the carboxyl group and the amine group also are useful for the tetrazole group. Therefore, one skilled in the art may refer to the text "Protective Groups in Organic Synthesis" (in particular, Chapters 5 and 7), Theodora W. Green, John Wiley & Sons, 1981, for the selection of other possible protecting groups that could be utilized for purposes of the present invention. Applicants hereby incorporate by reference the disclosure of this text for a more complete definition of the protecting group P.

The reaction is conducted in an aprotic solvent, for example, tetrahydrofuran, diethyl ether, toluene, benzene, dimethyl formamide, etc., at a temperature ranging from −70° C. to 25° C., preferably −30° C. to 0° C. Due to the moisture-sensitive nature of the reactants, the reaction is conducted in an inert atmosphere such as nitrogen.

The novel tetrazolylphenylboronic acid ($R^{1a}$ and $R^{1b}$=OH) can be isolated from the reaction mixture by the addition of water and maintaining the pH in the range of 3 to 8, preferably 5 to 6 with mineral acids such as phosphoric acid or carboxylic acid such as acetic acid.

The novel tetrazolylphenylboronic acid derivatives ($R^{1a}$ and $R^{1b}$=$C_1$–$C_4$ alkoxy, Cl, Br) can be used in step 2 without isolation.

In step 2, a novel compound prepared in step 1 is reacted with an electrophile having the formula

in a solvent in the presence of a metal catalyst and a base for two to thirty hours at a temperature ranging from room temperature to 150° C., preferably 60° to 90° C. The solvents for the reaction can be selected from a variety of known process solvents. Illustrative of solvent that can be utilized either singly or in combinations are benzene, toluene, ethyl ether, tetrahydrofuran, dioxane, acetonitrile, dimethylformamide, dimethylacetamide, ethanol, methanol, or propanol.

The metal catalyst is a complex of nickel, palladium, or platinum, preferably a palladium (O) complex such as tetrakistriphenylphosphine palladium. The active catalyst may be prepared in advance or generated in the reaction mixture. For example, addition of bis(dibenzylideneacetone)palladium to a reaction mixture containing triphenylphosphine generates the active triphenylphosphine palladium complex.

There are a variety of bases that can be used for effecting the reaction. Illustrative examples are organic tertiary non-nucleophilic bases such as triethylamine or diisopropylethylamine, inorganic bases such as potassium carbonate, sodium carbonate, thallium carbonate, potassium hydroxide, sodium hydroxide, thallium hydroxide, or the alkoxides of these alkali metals. When an inorganic base insoluble in the organic solvent is used, dissolution in water may be necessary; the use of a phase transfer catalyst such as tetra-n-butylammonium bromide or crown ether also facilitate the reaction. Organic solvent soluble bases such as tetra-n-butylammonium carbonate or hydroxide are particularly useful in certain cases.

Step 2 is such a general reaction that it tolerates a variety of functional groups as illustrated by literature examples (V. Snieckus, Chem. Rev., 1990, 90, 879–933 and references therein). Therefore, when Q has the previously given meaning W-L-, W may be any of various heterocyclic systems, including among others, imidazoles, triazolinones, quinazolinones, imidazolones, pyrazoles, pyrimidinones, or pyrroles. Accordingly, many of the AII receptor antagonists disclosed recently can be synthesized by the process disclosed in this invention. Applicants hereby incorporate by reference the disclosures of the following European Patent Office Applications for a more complete definition of the scope of heterocyclic systems that may be included as W in step 2 of the general reaction of this invention: EP 419048, EP 424317, EP 426021, EP 420237, EP 425921, EP 430300, EP 429257, EP 430709, EP 425211, EP 427463, EP 432737, EP 400974, EP 411766, EP 407342, EP 411507, EP 412848, EP 401030, EP 407102, EP 409332, EP 392317, EP 399731, EP 399732, EP 400835, EP 415886, EP 412594, EP 403158, EP 403159.

The invention is more fully exemplified and taught by the following examples.

EXAMPLE 1

2-(2'-Triphenylmethyl-2'H-tetrazol-5'-yl)phenylboronic acid

To a 22 L flask under nitrogen purge was charged 8.25 L acetone, followed by 1.1 kg 5-phenyltetrazole. Triethylamine (800 g) was added in such a rate that the temperature was maintained below 35° C. with some cooling. Solid trityl chloride was charged to this light suspension in five 440 g portions. The temperature was maintained below 35° C. An additional 1.38 L acetone was added to the reaction which was then maintained at 25° to 30° C. with stirring for 2 hours. Water (2.2 L) was added and the mixture was chilled to 15° to 20° C. The solid was collected by filtration; the filter cake was rinsed with 1.65 L 50% acetone-water followed by excess amount of water. The wet cake was re-slurried in 8 L acetone and 8 L of water was added slowly. The suspension was stirred for 1 hour then filtered. The filter cake was rinsed with 3 to 5 L of water. The white solid was dried in a vacuum oven at 40°–45° C. to a constant weight of 3.0 kg, mp 158°–160° C.

To a dry 12 L flask under nitrogen purge was charged 3.19 L of dry tetrahydrofuran. With agitation, 398 g of 5-phenyl-2-trityl-tetrazole prepared above was charged. The system was evacuated and released to nitrogen three times and then cooled to −20° C. A solution of butyl lithium in heptane (1.6M, 477 g) was then added to the reaction mixture while maintaining the temperature at −15° C. to −20° C. The resultant deep red solution was stirred at −5° C. for 1 hour during which time the lithium salt crystallized out. The solid suspension was cooled to −25° C. again and 333 g triisopropylborate was charged at a temperature range of −20° to −25° C. After the addition, the mixture was allowed to warm to 20° C. without heating. About 2.5 L of solvent was removed by vacuum distillation. The pot temperature was kept below 40° C. To the mixture was then added 2.66 L of 3% acetic acid and the resultant suspension was stirred for 1 hour. The white solid was collected by filtration. The solid cake was rinsed with 1.5 L of 20% tetrahydrofuran in water, followed by 3 L of water. The solid was dried under vacuum at room temperature to a constant weight of 502.3 g, mp 142°–146° C. (dec.).

EXAMPLE 2

3-(2'-Triphenylmethyl-2'H-tetrazol-5'-yl)phenylboronic acid m-Bromobenzonitrile (0.102 m) was dissolved in 130 mL of toluene and the solution was heated to boiling and 30 mL of solvent was distilled under nitrogen purge. After cooling down to room temperature, tri-n-butyl tin chloride (0.102 m) and sodium azide (0.1 m) were charged to the reaction and the mixture was heated at reflux for 18 hours. To the cooled down mixture was added 60 mL toluene and a solution of sodium hydroxide (0.12 m) in 12 mL water. After stirring at room temperature for 5 minutes, triphenylmethyl chloride (0.08 m) was added as a solid and the mixture was stirred for 1 hour. Another charge of triphenylmethyl chloride (0.02 m) was then made and the agitation continued for another hour. The reaction was worked up by addition of 50 mL water, basified with a small amount of sodium hydroxide. The layers were separated and the organic layer was extracted once with 50 mL water, followed by 50 mL saturated sodium chloride solution. The organic layer was dried over anhydrous sodium sulfate, filtered through celite and the filtrate was concentrated on a rotary evaporator. The residual oil was triturated with 200 mL of n-heptane and chilled in an ice bath. The solid was collected by filtration and rinsed with cold n-heptane. The filter cake was dried in a vacuum oven at 40° to 50° C. until constant weight.

The 2-triphenylmethyl-5-(m-bromophenyl)-2H-tetrazole obtained as described above is treated with n-butyllithium in tetrahydrofuran to generate the lithium salt of the carbanion, 2-triphenylmethyl-5-(m-lithiophenyl)-2H-tetrazole, which in turn is reacted with triisopropylborate to produce the title compound according to the procedure of Example 1.

EXAMPLE 3

4-(2'-Triphenylmethyl-2H-tetrazol-5'-yl)phenylboronic acid

Starting with p-bromobenzonitrile and using the procedure of Example 2, the title compound is prepared.

EXAMPLE 4

5-(4'-Methyl-1,1'-biphenyl-2-yl-2-triphenylmethyl-2H-tetrazole 2-(2'-Triphenylmethyl-2'H-tetrazol-5'-yl)phenylboronic acid (Example 1, 0.02 m = 9 g), p-bromotoluene (0.022 m = 3.84 g), sodium carbonate (0.04 m = 4.24 g), toluene (70 mL), and water (20 mL) were charged to a reaction flask. The system was evacuated and released to nitrogen three times and then maintained under a nitrogen atmosphere. Tetrakistriphenylphosphine palladium (0.6 mm = 0.693 g) was charged to the reaction mixture which was then heated at 80° C. for 10 hours. The reaction was cooled to room temperature. The organic layer was separated and extracted with 50 mL of water. The organic layer was dried over anhydrous sodium sulfate and concentrated. The residue was crystallized from toluene-n-heptane to give 6.76 g (71% yield) of title compound, mp 164°–166° C. (dec.).

EXAMPLE 5

5-(4'-Bromomethyl-1,1'-biphenyl-2-yl)-2-triphenylmethyl-2H-tetrazole

A mixture of 5-(4'-methyl-1,1'-biphenyl-2-yl)-2-triphenyl-2H-tetrazole (0.195 m = 93.5 g), N-bromosuccinimide (0.215 m = 38.2 g), VAZO®52 (2.37 g), and 563 g of methylene chloride was stirred and refluxed for 7 hours. The reaction mixture was cooled to room temperature and washed once with 375 mL of water, followed by a solution of 18.8 g of sodium bicarbonate in 357 mL of water. The methylene chloride solution was concentrated and the residue was triturated with 591 g of heptanes. The slurry was chilled to 0° C. before filtration. The solution was rinsed with 1:6 methylene chloride/heptanes and then dried in a vacuum oven at 50° C. to give 102.7 g of title compound.

EXAMPLE 6

2-n-Butyl-4-chloro-1-[(2'-(2-triphenylmethyl-2H-tetrazol-5-yl)-1,1'-biphenyl-4-yl)methyl]-1H-imidazole-5-carboxaldehyde A mixture of 5-(4'-bromomethyl-1,1'-biphenyl-2-yl)-2triphenylmethyl-2H-tetrazole (0.102 m = 63.1 g), 2-n-butyl-4-chloro-1H-imidazole-5-carboxaldehyde (0.113 m = 21.1 g) and anhydrous potassium carbonate (0.135 m = 18.6 g) in 251 g of N,N-dimethylacetamide was stirred at 0°–5° C. for 8 hours and the temperature of the reaction was raised to 25° C. for an additional 4 hours. Normally the product of this step was not isolated but reduced with sodium borohydride to give 2-n-butyl-4-chloro-1-[(2'-(2-triphenylmethyl-2H-tetrazol-5-yl)-1,1'-biphenyl-4-yl)methyl]-1H-imidazole-5-methanol. The title compound can be isolated by extraction into toluene from aqueous N,N-dimethylacetamide, concentration of the toluene solution, and crystallization from ethyl acetate or ethanol, mp 145°–147° C. (dec.).

EXAMPLE 7

2-n-Butyl-4-chloro-1-[(2'-(2-triphenylmethyl-2H-tetrazol-5-yl)-1,1'-biphenyl-4-yl)methyl]1H-imidazole-5-methanol To the reaction mixture of Example 6 was added sodium borohydride (0.1 m = 3.9 g) along with some water (8.7 mL). After stirring at room temperature for 3 hours, the reaction mixture was slowly added to excess amount of water (540 ml) with stirring. The wet filter cake was washed with 270 mL of water, then crystallized from 355 g of butyl chloride to give a crude product. Recrystallization from 300 g of ethyl acetate and dried in a vacuum oven to give 49.3 g of pure title compound in 72% yield for two steps, mp 168°–169° C.

EXAMPLE 8

2-n-Butyl-4-chloro-1-[(2'-(tetrazol-5-yl)-1,1'-biphenyl-4-yl)methyl]-1H-imidazole-5-methanol, potassium salt A mixture of 2-n-butyl-4-chloro-1-[(2'-(2-triphenylmethyl-2H-tetrazol-5-yl)-1,1'-biphenyl-4-yl)methyl]-1H-imidazole-5-methanol (5.3 kg) in 25 L tetrahydrofuran (THF) was treated with 8.38 kg of 12% aqueous hydrochloric acid added at 23° C. over an hour. The mixture was stirred at 25° C. for 12 hours. A 30% sodium hydroxide solution was added at 22° C. over a 2-hour period until the pH was 12.5. The THF was distilled off by heating but the volume was replenished by addition of water. Distillation was terminated when the head temperature reached 94° C. The mixture was cooled to room temperature and the precipitated triphenylmethanol was removed by filtration and rinsed with water. The filtrate and rinsing was extracted twice with 4 L portions of toluene. Ethyl acetate (9.8 L) was then added to the aqueous solution and 36% aqueous hydrochloric acid was added at 21°-24° C. until the pH was 3.8. The mixture was cooled to 10° C. and held for 1 hour. The solid was collected by filtration and washed with 50% aqueous methanol, followed by 10 L ethyl acetate, then dried at 50° C. in a vacuum oven to give 2.8 kg white solid, mp 182°-183° C. (dec.). A 1.92 kg portion of this solid in 5.8 kg of isopropanol was treated with a mixture of 0.363 kg of potassium hydroxide in 185 mL water and 3.62 L isopropanol at 0.363 kg of potassium hydroxide in 185 mL water and 3.62 L isopropanol at 39°-40° C. over a 4-hour period until the pH was 10. The solution was clarified by filtration. Approximately 67% of the water present was removed by distillation (monitored by Karl Fischer titration of the distillate). Heptanes (4.5 L) was added and the mixture was cooled to room temperature. The product was collected by filtration and rinsed with heptanes It was dried at 50° C. in a vacuum oven to yield 1.82 kg of white solid, mp 267°-269° C. (dec.).

EXAMPLE 9

5-(4'-Hydroxymethyl 1,1'-biphenyl-2-yl)-2-triphenylmethyl-2H-tetrazole

A mixture of 2-(2'-triphenylmethyl-2'H-tetrazol-5'-yl)phenylboronic acid (0.03 m=13.5 g), p-bromobenzyl alcohol (0.034 m=6.2 g) tetrabutylammonium carbonate (67% pure, 34 g), and 120 mL toluene in a reaction flask was evacuated and released to nitrogen three times and maintained under a nitrogen atmosphere. To the mixture was charged tetrakistriphenylphosphine palladium (0.9 mm=1.04 g). The reaction was heated at 75° to 81° C. for 5 hours. The reaction mixture was cooled to room temperature and extracted three times with 80 mL portions of water. The organic layer was clarified by filtering through a celite cake and then concentrated to a brown oil. Crystallization from about 30 mL of acetone yielded a solid which was collected and rinsed with 50% aqueous acetone. The solid was dried under a stream of nitrogen to a constant weight of 9.08 g (61.5% yield), mp 168°-170° C.

EXAMPLE 10

5-(4'-Methanesulfonyloxymethyl-1,1'-biphenyl-2-yl)-2-triphenylmethyl-2H-tetrazole To a mixture of 5-(4'-hydroxymethyl-1,1'-biphenyl-2-yl)-2-triphenylmethyl-2H-tetrazole (0.01 m=4.90 g) and potassium carbonate (0.05 m=6.90 g) stirred in 50 mL N,N-dimethylacetamide chilled at 1° C. was added a total of 3.34 g (0.024 m) of methanesulfonyl chloride in portions over 6 hours. The progress of the reaction was monitored by thin layer chromatography or HPLC. The title compound was formed in better than 90% in the mixture which was used in the next example.

EXAMPLE 11

2-n-Butyl-4-chloro-1-[(2'-(2-triphenylmethyl-2H-tetrazol-5-yl)-1,1'-biphenyl-4-yl)methyl]-1H-imidazole-5-methanol To the reaction mixture of Example 10 was added 2-n-butyl-4-chloro-1H-imidazole-5-carboxaldehyde (0.01 m=1.86 g). The reaction was stirred overnight at room temperature. Water (0.87 mL) was added dropwise followed by sodium borohydride pellets (0.37 g). After stirring for 5 hours, the reaction mixture was added slowly to 100 mL water containing 3 mL acetone. The temperature was maintained at about 25° C. during the addition. The resultant slurry was stirred for an additional 45 minutes, then filtered. The solid was rinsed with two 50 mL portions of water. The wet cake was recrystallized first from 50 mL of n-butyl chloride, then from 30 mL of ethyl acetate to give 1.95 g title compound in 28% overall yield; mp 168°-169° C.

EXAMPLE 12

5-(4'-Formyl-1,1'-biphenyl-2-yl)-2-triphenylmethyl-2H-tetrazole 2-(2'-Triphenylmethyl-2'H-tetrazol-5'-yl)phenyl boronic acid (5 mm=2.16 g), p-bromobenzaldehyde (6 mm=1.12 g), potassium carbonate (10 mm=1.38 g), tetrabutylammonium bromide (0.46 mm=0.15 g), toluene (20 mL), and water (1.2 mL) were charged to the reaction flask. The system was evacuated and released to nitrogen three times and then maintained under a nitrogen atmosphere. Tetrakistriphenylphosphine palladium (0.15 mm=0.18 g) was charged to the reaction mixture which was then heated at 70° to 80° C. for 5.5 hours. The cool reaction mixture was filtered to remove some solid; rinsed with toluene and water. The filtrate and rinsings were combined. The organic layer was separated and washed with 10 mL water, then dried over magnesium sulfate, filtered, and concentrated. The residue was triturated with a mixture of 8 mL toluene and 5 mL n-heptane. The solid was collected by filtration, rinsed with 1:1 toluene/n-heptane, and dried under vacuum is 1.18 g (48% yield), mp 147°-149° C.

EXAMPLE 13

1,1'-biphenyl-2-yl)-2-triphenylmethyl-2H-tetrazole 5-(4'-formyl-1,1'-biphenyl-2-yl)-2-triphenylmethyl-2H-tetrazole was dissolved in N,N-dimethylacetamide and some water and reduced by sodium borohydride. The reaction mixture was then poured into water slowly to precipitate the title compound which is further purified by recrystallizations as described in Example 11.

EXAMPLE 14

2-n-Butyl-4-chloro-1-p-bromobenzyl-1H-imidazole-5-carboxaldehyde

A mixture of 2-n-butyl-4-chloro-1H-imidazole 5-carboxaldehyde (0.6 m=111.9 g), p-bromobenzylbromide (0.6 m=153.02 g), anhydrous potassium carbonate (0.75 m=103.5 g), and dry N,N-dimethylacetamide (900 mL) was stirred at room temperature for 4 hours. The mixture was diluted with 1.2 L of toluene and 1.8 L of water. After mixing for half an hour, the layers were separated. The organic layer was washed two more times with 900 mL portions of water, then dried over magnesium sulfate. The drying agent was removed by filtration and the filtrate was concentrated. The residual oil was pumped overnight to a weight of 191.71 g (89.9% yield).

EXAMPLE 15

2-n-Butyl-4-chloro-1-[(2'-(2-triphenylmethyl-2H-tetrazol-5-yl)-1,1'-biphenyl-4-yl)methyl]-1H-imidazole-5-methanol A mixture of the oil obtained in Example 14 (0.05 m=17.8 g), 2-(2'-triphenylmethyl-2'H-tetrazol-5'-yl)phenylboronic acid (0.065 m=29.3 g), potassium carbonate (0.1 m=13.8 g), water (11 mL), tetra-n-butylammonium bromide (0.005 m=1.61 g), triphenylphosphine (0.006 m=1.58 g) in 200 mL toluene was evacuated and released to nitrogen three times and maintained under a nitrogen atmosphere. Tris(dibenzylideneacetone)dipalladium (1.5 mm=0.64 g) was charged and the reaction was heated at 75° to 81° C. for 12 hours. The cooled reaction mixture was filtered to remove some grey solid. The toluene layer was stirred with sodium borohydride (0.1 m=3.8 g), tetra-n-butyl ammonium bromide (0.005 m=1.6 g), and 30 mL water for six hours. The mixture was filtered through a celite cake to remove the black tarry precipitate. The organic layer was washed once with 100 mL water then stirred with a solution of thiourea (7 g) in 100 mL water for 1 hour. Some brown sludge (palladium complex) was formed and precipitated out. The mixture was filtered and the organic layer was separated then treated with a fresh solution of thiourea (7 g) in 100 mL water for 1 hour. The organic layer was separated, washed once with 100 mL water and once with 100 mL saturated sodium chloride solution. The organic layer was stirred with 30 g magnesium sulfate and 15 g charcoal for 1 hour. The solid was removed by filtering through a celite cake. The filtrate was concentrated to an oil and crystallized from 35 mL of isobutyl acetate in an ice bath. The solid was collected and dried under a stream of nitrogen to a constant weight of 17.17 g.

EXAMPLE 16

2-n-Propyl-4-ethyl-1-[(2'-(2-triphenylmethyl-2H-tetrazol-5-yl)-1,1'-biphenyl-4-yl)methyl]-1H-imidazole-5-carboxaldehyde Starting with 2-n-propyl-4-ethyl-1H-imidazole-5-carboxaldehyde and using the procedure of Example 14 and then the procedure of Example 12, the title compound is prepared.

EXAMPLE 17

2-n-Propyl-4-pentafluoroethyl-1-[(2'-(2-triphenylmethyl-2H-tetrazol-5-yl)-1,1'-biphenyl-4-yl)methyl]-1H-imidazole-5-carbomethoxylate Starting with 2-n-propyl-4-pentafluoroethyl-1H-imidazole-5-carbomethoxylate and using the procedure of Example 14 and then the procedure of Example 12, the title compound is prepared.

What is claimed is:

1. A compound of formula I

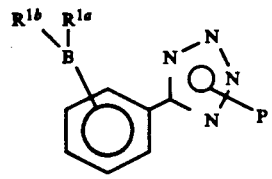

wherein:

P is triphenylmethyl, tertiary-butyl, $C_1$–$C_4$ alkoxymethyl, methylthiomethyl, phenyl $C_1$–$C_4$ alkoxymethyl, p-methoxybenzyl, 2,4,6-trimethylbenzyl, 2-(trimethylsilyl)ethyl, tetrahydropyranyl, piperonyl, or benzenesulfonyl; and $R^{1a}$ and $R^{1b}$ are each independently chlorine, bromine, $C_1$–$C_4$ alkoxy or hydroxy; and $R^{1a}$ and $R^{1b}$ can be taken together with B to form a cyclic structure

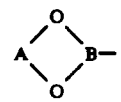

where A is phenyl, or $(CH_2)_n$, where n is 2–4.

2. A compound of claim 1 wherein $R^{1a}$ and $R^{1b}$ are hydroxyl.

3. A compound of claim 1 wherein P is a triphenylmethyl.

4. A compound of claim 1 which is 2-(2'-triphenylmethyl-2'H-tetrazol-5'-yl)phenylboronic acid.

5. A compound of claim 1 which is 3-(2'-triphenylmethyl-2'H-tetrazol-5'-yl)phenylboronic acid.

6. A compound of claim 1 which is 4-(2'-triphenylmethyl-2'H-tetrazol-5'-yl)phenylboronic acid.

* * * * *

UNITED STATES PATENT AND TRADEMARK OFFICE
CERTIFICATE OF CORRECTION

PATENT NO. : 5,130,439
DATED : July 14, 1992
INVENTOR(S) : Young S. Lo, 516 Stenning Dr., Hockessin, Del. 19707; Lucius T. Rossano, 7 West Ridge Ct., Newark, Del. 19711

It is certified that error appears in the above—identified patent and that said Letters Patent is hereby corrected as shown below:

On the title page, Item [76] should read as follows:
—Young S. Lo, 516 Stenning Dr., Hockessin, Del. 19707—

Signed and Sealed this

Twelfth Day of October, 1993

Attest:

BRUCE LEHMAN

*Attesting Officer*    *Commissioner of Patents and Trademarks*